United States Patent
Nagarajan

(10) Patent No.: US 11,445,940 B2
(45) Date of Patent: Sep. 20, 2022

(54) SYSTEM AND METHOD FOR TRACKING PERFORMANCE OF PHYSICAL ACTIVITY OF A USER

(71) Applicant: Bharath Nagarajan, Bangalore (IN)

(72) Inventor: Bharath Nagarajan, Bangalore (IN)

(*) Notice: Subject to any disclaimer, the term of this patent is extended or adjusted under 35 U.S.C. 154(b) by 332 days.

(21) Appl. No.: 16/767,104

(22) PCT Filed: Nov. 27, 2018

(86) PCT No.: PCT/IN2018/050790
§ 371 (c)(1),
(2) Date: May 26, 2020

(87) PCT Pub. No.: WO2019/102498
PCT Pub. Date: May 31, 2019

(65) Prior Publication Data
US 2020/0305767 A1  Oct. 1, 2020

(30) Foreign Application Priority Data
Nov. 27, 2017  (IN) .............................. 201741042457

(51) Int. Cl.
*A61B 5/11* (2006.01)
*G16H 20/30* (2018.01)
*B64C 39/02* (2006.01)

(52) U.S. Cl.
CPC ........... *A61B 5/1128* (2013.01); *A61B 5/1112* (2013.01); *B64C 39/024* (2013.01); *G16H 20/30* (2018.01); *A61B 2503/10* (2013.01); *A61B 2562/0219* (2013.01); *B64C 2201/127* (2013.01); *B64C 2201/141* (2013.01); *B64C 2201/146* (2013.01)

(58) Field of Classification Search
CPC combination set(s) only.
See application file for complete search history.

(56) References Cited

U.S. PATENT DOCUMENTS

| | | |
|---|---|---|
| 2016/0136482 A1 | 5/2016 | Askew, Jr. et al. |
| 2017/0161561 A1 | 6/2017 | Marty et al. |
| 2019/0135450 A1* | 5/2019 | Zhou .................... G05D 1/0016 |

* cited by examiner

*Primary Examiner* — Michael V Kerrigan

(57) ABSTRACT

A system and method for tracking performance of a physical activity of a user on a field are provided. The system comprises a visual aid unit and a controller. The controller is configured to receive sensor data indicative of at least one of position and direction of movement of the user on the field. The sensor data is generated in relation to a first performance of the physical activity by the user. The controller analyzes the sensor data to generate visual indicators for the user. The controller controls the visual aid unit to project the generated visual indicators during a second performance of the physical activity by the user for reference of the user. The visual indicators are configured to aid in improving the performance of the user in relation to the physical activity.

20 Claims, 4 Drawing Sheets

SYSTEM AND METHOD FOR TRACKING PERFORMANCE OF PHYSICAL ACTIVITY OF A USER

CROSS REFERENCE TO RELATED APPLICATIONS

This application claims priority to Indian provisional patent application No. 201741042457, filed Nov. 27, 2017, which is incorporated herein in its entirety by this reference thereto.

TECHNICAL FIELD

The present technology generally relates to training equipment in use for physical activities and, more particularly, to a system and method for tracking performance of physical activity of a user.

BACKGROUND

Athletics has become an integral part of society. With greater general attention on athletics comes greater attention on improving athletic performance Today's athletes, beginning as early as the elementary school level, specialize in particular areas and train year-round to improve their skills and their conditioning. With athletics leading to a possibly lucrative career for some, and to academic assistance in the form of scholarships to others, more and more athletes have looked to improve their performance by training harder and harder. Such training may involve capturing data related to athlete's two successive performances and comparing the data to find out if the athlete's later performance has improved over his/her initial performance or not. Traditionally, such analysis (comparison) is completed after the performances, therefore the athlete does not get opportunity to know about improvement/shortcomings (if any) of the later performance in consideration of the initial performance while training. For instance, in the sport of sprinting, the athlete may like to know if his/her later run produced better timings as compared to his/her initial run and may even prefer to have real-time feedback about his/her shortcomings during the run, so the athlete can know at what stage (section) of the run he/she needs to push more for achieving better results.

Some athletes hire a coach who can compare athlete's successive performances in real-time and provide observations related to comparison. A talented coach can often observe subtle shortcomings in an athlete's performance and can direct the player to correct those shortcomings. Despite the talent and the experience obtained by many top coaches or athletic experts, human perception can only capture a small subset of the factors that affect an athlete's performance in real-time. The most highly skilled trainers and coaches still do not have the ability to quantify very small differences in motion, for example, between two sprint runs from same athlete, due to usually there being fraction of seconds difference between the two performances. These differences in motion can be the most important elements in comparing and diagnosing a player's skill. Furthermore, hiring such professional coaches for regular training activities can be expensive. Also, the busy schedules of many talented coaches make it difficult for these individuals to set aside time to meet with an athlete on a routine basis. Thus, many individual athletes forego using the services of professional coaches.

Moreover, sprinting or running has always been one of the most difficult sports to measure performance, owing to the accuracy demanded by timers. Current timing systems are available to measure the running speed and distances but are usually bulky, hard to deploy and are difficult transport. Further, some of the systems which are used to measure speed and time needs to be built into the track, such as pressure sensors in the start position and end, and infra-red timing gates located along the track. This makes it difficult for an individual athlete to always have performance data during training, due to unavailability of sensor-fitted track during training time.

Therefore, there is a need to provide real-time feedback to the user about a physical activity, while the physical activity is being performed. It would also be advantageous to provide the real-time feedback using a device, which is easy to deploy and is easily transportable so as to be employed by a user for measuring performance of a physical activity.

SUMMARY

In an embodiment of the invention, a system for tracking performance of a physical activity of a user on a field is disclosed. The system includes a visual aid unit and a controller. The controller is in operable communication with the visual aid unit. The controller receives sensor data indicative of at least one of position and direction of movement of the user on the field. The sensor data is generated in relation to a first performance of the physical activity by the user. The controller is configured to analyze the sensor data to generate visual indicators for the user. The controller is further configured to control the visual aid unit to project the generated visual indicators during a second performance of the physical activity by the user for reference of the user. The visual indicators are configured to aid in improving the performance of the user in relation to the physical activity.

In an embodiment of the invention, a computer-implemented method for tracking performance of a physical activity of a user on a field is disclosed. The method includes receiving, by a system, sensor data indicative of at least one of position and direction of movement of the user on the field. The sensor data is generated in relation to a first performance of the physical activity by the user. The method includes analyzing, by the system, the sensor data to generate visual indicators for the user. The method includes projecting, by the system, the generated visual indicators during a second performance of the physical activity by the user for reference of the user. The visual indicators are configured to aid in improving the performance of the user in relation to the physical activity.

In an embodiment of the invention, an unmanned vehicle for tracking performance of a physical activity of a user on a field is disclosed. The unmanned vehicle is capable of traversing the field. The unmanned vehicle includes a visual aid unit, a communication unit and a controller. The communication unit is in operable communication with an electronic device associated with the user for receiving sensor data indicative of at least one of position and direction of movement of the user on the field. The sensor data is generated in relation to a first performance of the physical activity by the user. The controller is in operable communication with the visual aid unit and the communication unit. The controller is configured to analyze the sensor data to generate visual indicators for the user. The controller controls the unmanned vehicle to traverse the field based, at least in part, on the sensor data to effectively follow the direction of the movement of the user during a second performance of the physical activity by the user. The controller is configured to control the visual aid unit to project the generated visual indicators during the second performance of the physical activity by the user for reference of the user. The visual indicators are configured to aid in improving the performance of the user in relation to the physical activity

DETAILED DESCRIPTION

The detailed description provided below in connection with the appended drawings is intended as a description of the present examples and is not intended to represent the only forms in which the present example may be constructed or utilized. However, the same or equivalent functions and sequences may be accomplished by different examples.

Figure 1:
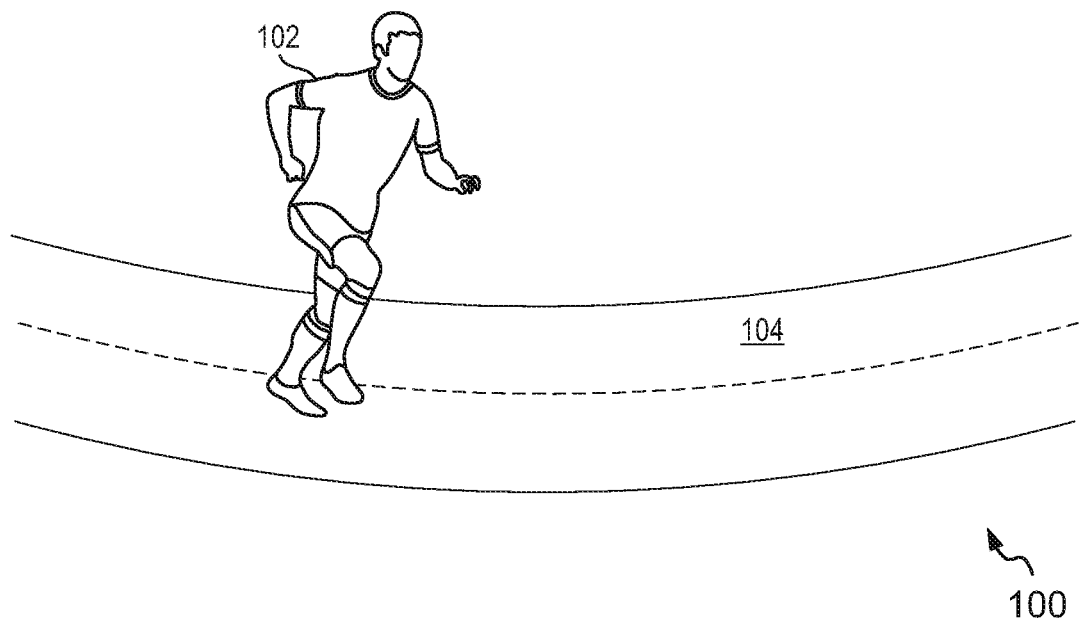
FIG. 1 shows an example representation of a user engaged in a physical activity, in accordance with an example scenario.

FIG. 1 shows an example representation 100 of a user 102 engaged in a physical activity, in accordance with an example scenario. The user 102 is exemplarily depicted to be engaged in a sprinting activity on a track field 104. It is noted that the physical activity of the user 102 is depicted to be a sprinting activity for illustration purposes. The user 102 may engage in other types of physical activities such as jogging or running, swimming, engaging in a high jump or a long jump activity, and the like.

In many example scenarios, the user 102 may wish to track a his/her performance in relation to the physical activity. For example, the user 102 may wish to track the sprint performance at different stages of the sprinting activity. More specifically, the user 102 may wish to track various parameters such as number of steps taken to cover the first 50 meters for instance, an average step size, a position of the head at the end of completing the race, and so on and so forth. Conventional mechanisms for tracking performance of physical activities require a range of devices to provide performance data to the user 102. For example, pressure sensors fitted in the track field 104 may provide information related to the step size and the number of steps taken during a sprint performance, whereas, stopwatches and infra-red gates may assist in estimating the overall timing and the head position during the completion of the sprint. In addition to requiring a range of devices to provide performance data to the user 102, conventional mechanisms are configured to provide the performance data only subsequent to performance of the physical activity. There is no mechanism to provide real-time feedback to the user 102 while the user 102 is performing the physical activity.

Various embodiments of the present invention provide a system and method that are capable of overcoming these and other obstacles and providing additional benefits. More specifically, various embodiments of the present invention disclosed herein provide techniques for tracking performance of physical activity of users, such as the user 102. Moreover, the techniques disclosed herein are configured to provide real-time feedback to a user while the user is performing the physical activity. An example system for tracking performance of physical activity of the user is explained with reference to FIG. 2.

Figure 2:
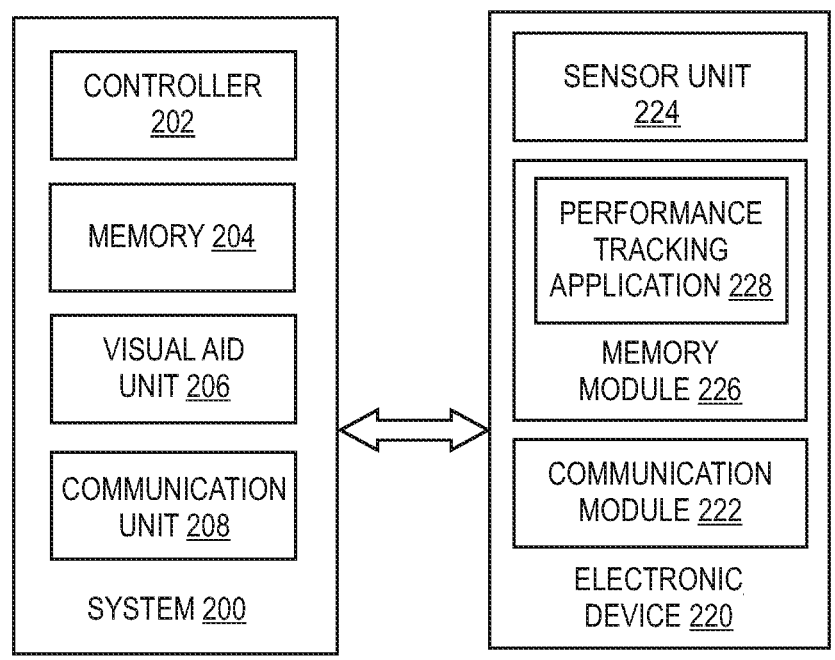
FIG. 2 shows a block diagram representation of a system configured to track performance of physical activity of a user, in accordance with an embodiment of the invention.

FIG. 2 shows a block diagram representation of a system 200 configured to track performance of physical activity of a user, in accordance with an embodiment of the invention. For the purposes of the present invention, the physical activity may be any competitive or professional sport which may require training on part of the user to achieve maximum performance. Embodiments of the present invention have been described in terms of sprinting or running being considered as the physical activity of the user; however, the physical activity of the user for the purposes of the present invention may include any form of sport or exercise being performed by the user.

An example user of the system 200 may be an athlete, a sports coach or any individual interested in tracking and improving performance for a chosen physical activity. In at least one embodiment, the system 200 may be deployed in another device, such as an unmanned vehicle for example, which is capable of traversing the field so as to follow the user while the user is performing a physical activity. Alternatively, in some embodiments, the system 200 may be deployed in a stationary standalone device and configured to project visual indicators proximal to the user, while the user is performing the physical activity as will be explained in further detail later.

The system 200 is depicted to include a controller 202, a memory 204, a visual aid unit 206 and a communication unit 208. In an embodiment, the memory 204 is capable of storing machine executable instructions, referred to herein as platform instructions. Further, the controller 202 is capable of executing the platform instructions. In addition to the platform instructions, the memory 204 is configured to store instructions for analysis of sensor data and imaging data. In at least some embodiments, the memory 204 is further configured to store instructions for generating visual indicators based on the analysis of the sensor data. In an illustrative example, the controller 202 may use the instructions to analyze the sensor data generated corresponding to a sprinting activity of the user and generate visual indicators such as images of footsteps of the user as the user progresses during the sprinting activity. In another illustrative example, a visual indicator such as a line indicating a position of the user during various stages of the sprinting activity may be generated. The visual indicators may be projected during a subsequent performance of the physical activity so as to provide real-time feedback (vis-à-vis a previous performance) to the user while the user is performing the physical activity.

In an embodiment, the controller 202 may be embodied as a multi-core processor, a single core processor, or a combination of one or more multi-core processors and one or more single core processors. For example, the controller 202 may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like. In an embodiment, the controller 202 may be configured to execute hard-coded functionality. In an embodiment, the controller 202 is embodied as an executor of software instructions, wherein the instructions may specifically configure the controller 202 to perform the algorithms and/or operations described herein when the instructions are executed.

The memory 204 may be embodied as one or more volatile memory devices, one or more non-volatile memory devices, and/or a combination of one or more volatile memory devices and non-volatile memory devices. For example, the memory 204 may be embodied as semiconductor memories (such as mask ROM, PROM (programmable ROM), EPROM (erasable PROM), flash memory, RAM (random access memory), etc.), magnetic storage devices (such as hard disk drives, magnetic tapes, etc.) and the like.

In at least some embodiments, the visual aid unit 206 may be embodied as a laser or some other optical projection means which can project visual indicators, such as a line, on the field for the reference of the user. For example, the visual aid unit 206 may be oriented (due to rotation/orientation of the system 200 or the unmanned vehicle in which the system 200 is deployed) so as to project laser beams in the form of a straight line (or even in the form of a point) proximal to, or specifically adjacent to, the user (like in front and/or sides of the user) while the user is, say, running for providing visual indicators about a running path which the user can then follow. In another example, the visual aid unit 206 may be in the form of a screen which may be supported by the unmanned vehicle while traversing the field, such that the said screen is always in front of the user showing real-time visual feedback or indicators about the physical activity to the user.

The visual aid unit 206 is controlled by the controller 202. More specifically, the controller 202 provides the visual indicators generated based on the analysis of the sensor data to the visual aid unit 206, which in turn may be configured to project the visual indicators on a portion of the field proximal to the user, while the user is performing the physical activity. For example, visual indicators, such as images of footsteps or a line indicating a position of the user during a previous sprint performance, may be projected on the field and the projections may progress along with the user while the user is sprinting.

The communication unit 208 is configured to facilitate communication between the system 200 and one or more remote devices, such as one or more electronic devices of the user. To that effect, the communication unit 208 may include communication circuitry such as for example, a transceiver circuitry including antenna and other communication media interfaces. In an illustrative example, the communication unit 208 may enable the system 200 to connect to a communication network, such as a cellular network, a wireless LAN, a Bluetooth or ZigBee network, and the like, to facilitate communication with the remote devices, such as a user's electronic device. An example representation of user's electronic device 220 is shown as block 220 in FIG. 2. The electronic device 220 may be embodied as a wearable unit, like a band or a belt, which may be worn by the user during the physical activity. In other examples, the electronic device 220 may be embodied as a smartphone or any small device which may be carried by the user in his/her pocket. The electronic device 220 is depicted to include a communication module 222, a sensor unit 224 and a memory module 226 storing a performance tracking application 228. It is understood that the electronic device 220 may include several other components than those depicted in FIG. 2. For example, the electronic device 220 may include a multi-core processor, a display screen, etc., which are not shown in FIG. 2.

The communication module 222 may include transmitter/receiver circuitry similar to the communication circuitry associated with the communication unit 208. The communication module 222 facilitates connection of the electronic device 220 to communication network so as to facilitate communication with remote machines such as the system 200.

In an embodiment, the sensor unit 224 includes instruments or measuring devices capable of, generally, measuring a location and movement of the user on the field, while the user is performing the physical activity. Further, the sensor unit 224 is configured to generate sensor data indicative of one or more of positions and direction of movement of the user on the field. To that effect, the sensor unit 224 includes one or more inertial sensors and position sensors for measuring position and direction of movement of the user on the field. With use of inertial sensors, like an accelerometer and/or a gyroscope, the sensor unit 224 can measure precise movement of the user on the field. Further, in one example, the position sensors may use one or more of Global Positioning System (GPS), Global Navigation Satellite System (GLONASS), Galileo, BeiDou Navigation Satellite System and Indian Regional Navigation Satellite System (IRNSS) to measure precise location of the user on the field. Such measurement techniques are known in the art and thus have not been described herein for brevity of the present invention. It may be appreciated that many other types of sensors may be applicable of providing such position and movement measurements, and the sensor unit 224 could employ any such types of sensors without any limitations.

The one or more sensors in the sensor unit 224 are configured to sense motion/movement of the user and generate sensor data, such as for example, inertial movement information and location information of the user on the field. In at least one embodiment, the position and the direction of the movement of the user may be determined based on the sensor data generated by the one or more sensors in the sensor unit 224.

In at least one embodiment, the performance tracking application 228 may be an application associated with the system 200 and installed in the electronic device 220 by the user from an application store (or the performance tracking application 228 may even be pre-installed in the electronic device 220). The performance tracking application 228 may be configured to collate the sensed information from the sensors in the sensor unit 224 and provision the information to the communication unit 208 of the system 200. In at least some embodiments, the communication between the sensors in the sensor unit 224 and the performance tracking application 228 may be initiated using application programming interface (API) calls.

The various components of the system 200, such as the controller 202, the memory 204, the visual aid unit 206 and the communication unit 208 are configured to communicate with each other via or through a centralized circuit system (not shown in FIG. 2). The centralized circuit system may be various devices configured to, among other things, provide or enable communication between the components (202-208) of the system 200. In certain embodiments, the centralized circuit system may be a central printed circuit board (PCB) such as a motherboard, a main board, a system board, or a logic board. The centralized circuit system may also, or alternatively, include other printed circuit assemblies (PCAs) or communication channel media. It is noted that though the various components of the system 200 are depicted to be integrated within a single device, in at least some embodiments, the system 200 may be configured as a distributed system with its individual components being separately disposed and in communication with each other to monitor performance of the physical activity of the user and to provide real-time feedback thereto for aiding in improving performance of the user in relation to the physical activity without departing from the scope of the present invention.

As explained above, the system 200 may be deployed in another device, such as an unmanned vehicle for example, which is capable of traversing the field so as to follow the user while the user is performing a physical activity. An example representation of the system 200 located in an unmanned vehicle is shown in FIG. 3.

Figure 3:
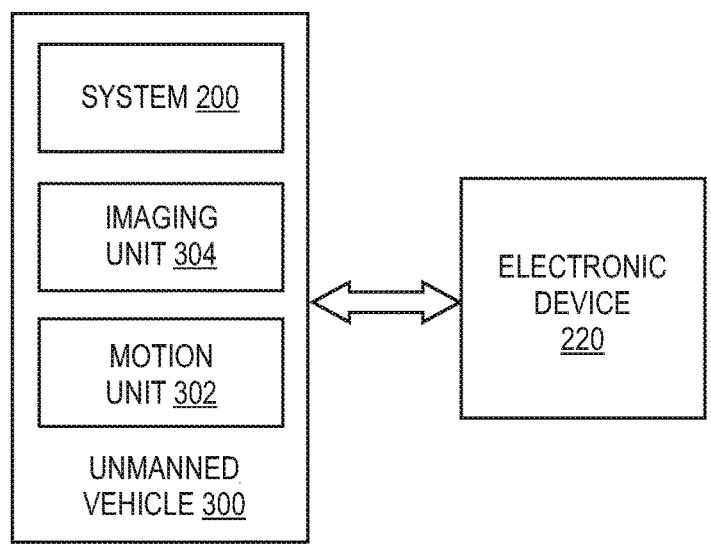
FIG. 3 shows a block diagram representation of an unmanned vehicle including the system of FIG. 2, in accordance with an embodiment of the invention.

FIG. 3 shows a block diagram representation of an unmanned vehicle 300 including the system 200 of FIG. 2, in accordance with an embodiment of the invention. The unmanned vehicle 300 may be any driverless or pilotless vehicle which can follow the movement of the user on the field in a generally smooth and efficient manner. In at least one example embodiment, the unmanned vehicle 300 is an unmanned aerial vehicle (also known as UAV or a drone). The unmanned aerial vehicle may include a number of rotors, which may for example be propellers, and which render the unmanned aerial vehicle capable of controlled flight. In one embodiment, the present unmanned aerial vehicle may have four propellers (and may accordingly be referred to as 'quadcopter' or 'quadrotors') which may provide sufficient stability to the unmanned aerial vehicle to be able to properly follow the user, as required. In one implementation, the quadrotors are 200 mm class race drones capable of fast flight and fitted with barometers, accelerometers, GPS modules and the like for stable flight operations. In the unmanned aerial vehicle, the propellers are mounted to a body of the unmanned aerial vehicle and are arranged to rotate relative thereto. When rotated, the propellers provide lift to the unmanned aerial vehicle, allowing it to fly. It may be appreciated that, although, the present embodiments have been described in terms of the unmanned vehicle 300 being an unmanned aerial vehicle; in other implementations, the unmanned vehicle 300 may be a ground vehicle, such as a land robot or the like, which can travel with sufficient pace and maneuverability to follow the user on the field while the user is performing the physical activity.

The unmanned vehicle 300 is depicted to include the system 200 explained with reference to FIG. 2 and not explained again herein. The unmanned vehicle 300 is further depicted to include a motion unit 302 and an imaging unit 304. The motion unit 302 may include one or more components such as rotor blades with associated circuitry for facilitating motion of the unmanned vehicle 300. For example, the motion unit 302 is configured to enable the unmanned vehicle 300 to traverse a field (such as for example, a sprinting track). The imaging unit 304 may be embodied as a motion camera capable of recording the physical activity of the user. For example, the imaging unit 304 may be configured to capture one or more images (for example, individual image frames or a sequence of image frames in form of video) corresponding to the user's physical activity. It may be appreciated that since the unmanned vehicle 300 may follow the movement of the user on the field, thus the user may always be in frame for recording by the imaging unit 304 installed thereon. It is noted that the unmanned vehicle 300 may include several other components, such as power circuitry, memory storage, and the like, which are not shown herein.

In at least one example embodiment, the unmanned vehicle 300 is programmed to traverse the field along with the user (preferably in the front of the user or adjacent to the user) during a first performance of the physical activity. For example, the unmanned vehicle 300 embodied as a drone may fly in front of the user while the user is sprinting on the track field. The sensor data corresponding to the first performance is generated by the sensor unit 224 in the electronic device 220 and collated by the performance tracking application 228 and transmitted to the communication unit 208 in the system 200 deployed in the unmanned vehicle 300. The controller 202 in the system 200 is configured to analyze the sensor data to generate visual indicators (such as the visual indicators explained with reference to FIG. 2). In some embodiments, imaging data generated by recording the first performance may also be analyzed along with the sensor data to generate the visual indicators. During the second performance of the physical activity, the controller 202 is configured to control the unmanned vehicle 300 to traverse the field based, at least in part, on the sensor data to effectively follow the direction of the movement of the user during the second performance of the physical activity. More specifically, the unmanned vehicle 300 is programmed to fly by the controller 202 at a variable speed at least in part on the sensor data corresponding to the first performance of the physical activity. The controller 202 may further be configured to control the visual aid unit 206 to project the generated visual indicators on the field proximal to the position of the user during the second performance of the physical activity to serve as a reference for the user. Such a real-time feedback of performance during the second performance vis-à-vis the first performance may aid in improving the performance of the user in relation to the physical activity. Such tracking of performance is further explained with reference to FIG. 4.

Figure 4:
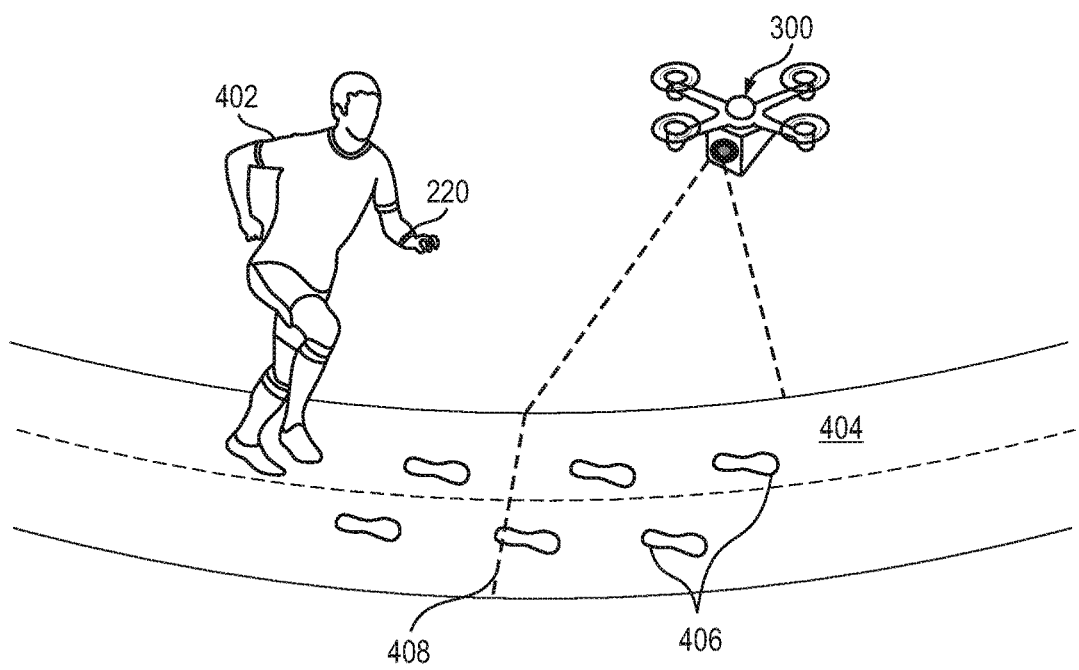
FIG. 4 shows an example representation of a user for illustrating a tracking of performance of a sprinting activity of the user 402, in accordance with an embodiment of the invention.

FIG. 4 shows an example representation of a user 402 for illustrating a tracking of performance of a sprinting activity of the user 402, in accordance with an embodiment of the invention. The user 402 is depicted to be engaged in a sprinting activity for illustration purposes. More specifically, the user 402 is depicted to be running on a field 404. The field 404 may be any outdoor track or any piece of land on which the user 402 may run. Alternatively, the field 404 may be an indoor track or the like without any limitations.

In at least one embodiment, during a first sprint performance, the unmanned vehicle 300 (explained with reference to FIG. 3 and not explained again herein) is set to mirror the movements of the user 402, as the inertial sensors included within the electronic device 220 sends continuous input to the unmanned vehicle 300. Thus, when the user 402 runs, the unmanned vehicle 300 flies in proximity of the user 402. At the end of the run, the details of the flight, the imaging data and the sensor data are stored in the memory 204 of the system 200 (shown in FIG. 2). The controller 202 of the system 200 (the controller is shown in FIG. 2) may then analyze the sensor data received from the electronic device 220 and other related data to generate visual indicators, such as the visual indicators explained with reference to FIG. 2.

Thereafter, during the second sprint performance, the controller 202 may control the unmanned vehicle 300 to traverse the field 404 based, at least in part, on the sensor data to effectively follow direction of movement of the user 402 during the second sprint performance. Further, the controller 202 controls the visual aid unit 206 (not shown in FIG. 4) to project the generated visual indicators (shown as footsteps 406 and a dotted line 408) on the field proximal to the position of the user 402 thereon for reference thereof while the physical activity (i.e. the second sprint performance) is being performed by the user 402. For example, once the sprint data is stored for the first sprint performance, the user 402 now takes the second run where the unmanned vehicle 300 flies in sync supplemented with laser beams from the visual aid unit 206, mirroring the run speed of the user's previous performance (the previous flight recorded), thereby providing the user 402 with real-time visual feedback in the form of comparison between the two user's running performances. In another embodiment, the unmanned vehicle 300 may include the pre-recorded data of past runs and use the pre-recorded data to project the laser beams as visual reference points to the user 402. In yet another embodiment, the unmanned vehicle 300 may project multiple laser beams which are reference of one or more past runs, best runs or pre-defined targeted run speed. This enables the user 402 to face his/her own past performances in real-time and leads to improved performance during the run itself. It is noted that in some embodiments, the system 200 may be deployed in a stationary device and mounted along with one or more cameras on a rigging, oriented at the user 402 to observe the user 402 performing the action and the outcome of the action each time the action is performed.

A method for improving performance of physical activity of a user is explained next with reference to FIG. 5.

Figure 5:
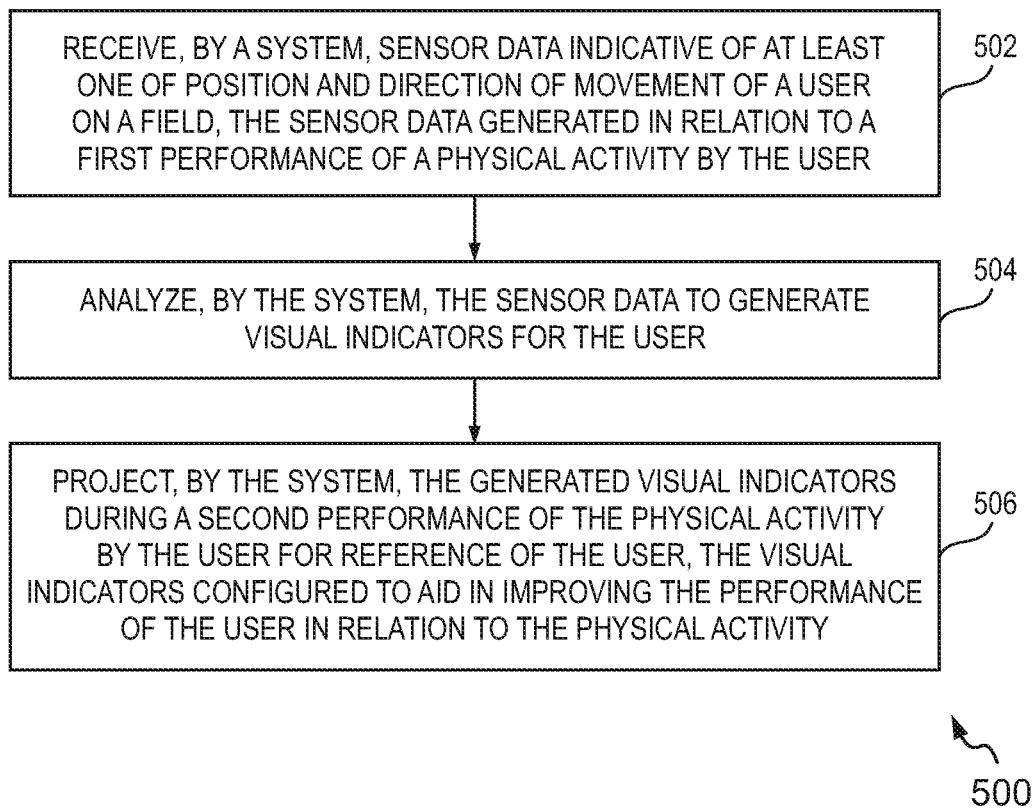
FIG. 5 is a flow diagram of an example method for tracking performance of a physical activity of a user on a field, in accordance with an embodiment of the invention.

FIG. 5 is a flow diagram of an example method 500 for tracking performance of a physical activity of a user on a field, in accordance with an embodiment of the invention. The method 500 depicted in the flow diagram may be executed by, for example, the system 200 explained with reference to FIGS. 2 to 4. Operations of the flowchart, and combinations of operation in the flowchart, may be implemented by, for example, hardware, firmware, a processor, circuitry and/or a different device associated with the execution of software that includes one or more computer program instructions. The operations of the method 500 are described herein with help of the system 200. It is noted that, the operations of the method 500 can be described and/or practiced by using any system other than the system 200. The method 500 starts at operation 502.

At operation 502 of the method 500, sensor data indicative of at least one of position and direction of movement of a user on the field is received by a system, such as the system 200. As explained with reference to FIGS. 2 to 4, a sensor unit, such as the sensor unit 224 shown in FIG. 2, deployed in an electronic device of the user is configured to generate sensor data. The sensor unit may include at least one inertial sensor and at least one position sensor to generate inertial position information and location information corresponding to the physical activity of the user. The sensor data is generated in relation to a first performance of the physical activity by the user.

At operation 504 of the method 500, the sensor data is analyzed to generate visual indicators for the user by the system. In an illustrative example, the system may analyze the sensor data generated corresponding to a sprinting activity of the user and generate visual indicators such as images of footsteps of the user as the user progresses during the sprinting activity. In another illustrative example, a visual indicator such as a line indicating a position of the user during various stages of the sprinting activity may be generated.

At operation 506 of the method 500, the generated visual indicators are projected for reference of the user during a second performance of the physical activity of the user. Projected the visual indicators during a subsequent performance of the physical activity provides real-time feedback (vis-à-vis a previous performance) to the user while the user is performing the physical activity. As such, the visual indicators is configured to aid in improving the performance of the user in relation to the physical activity.

The method 500 ends at operation 506.

Figure 6:
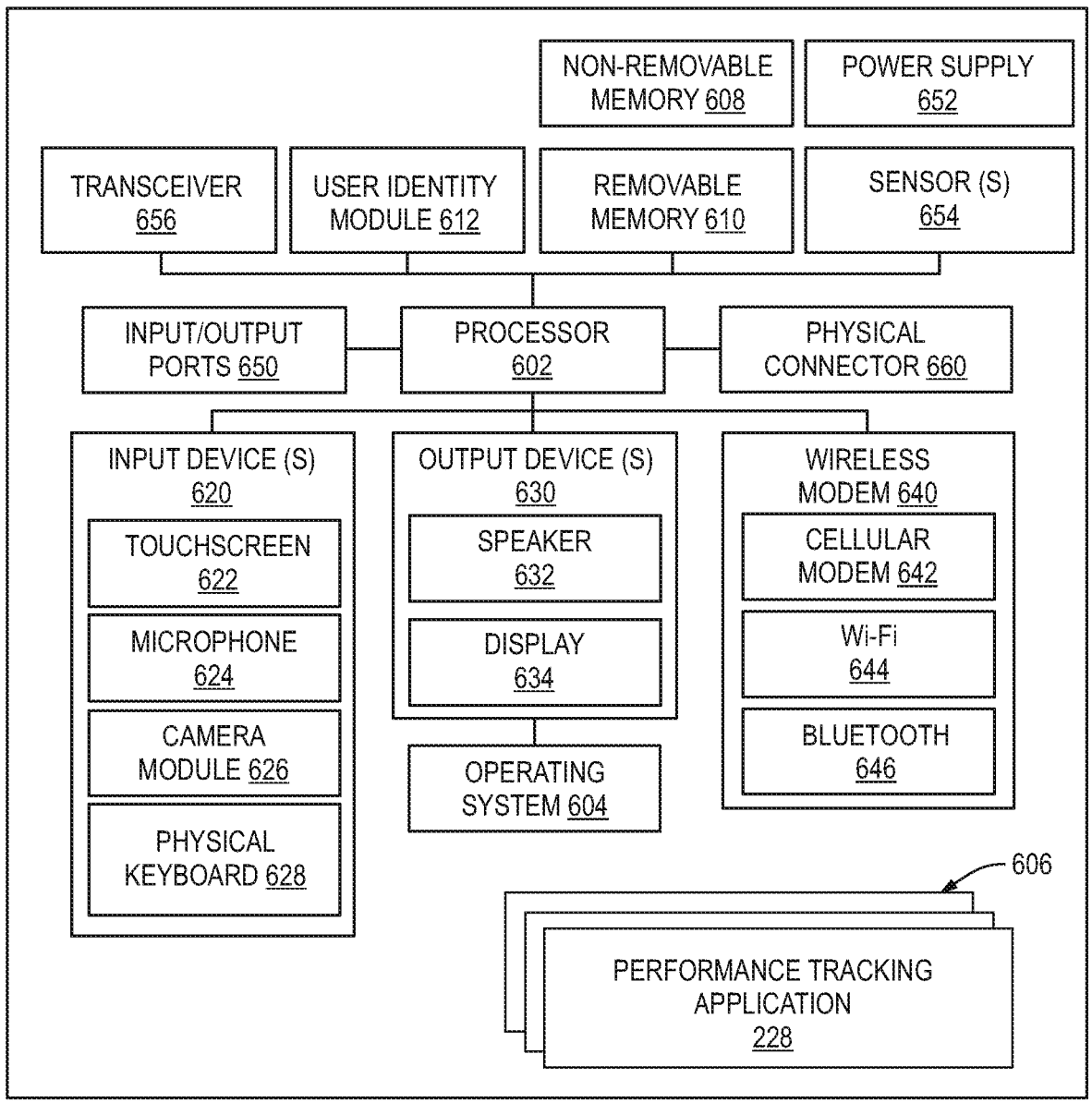
FIG. 6 shows simplified block diagram of an electronic device in accordance with an embodiment of the invention.

FIG. 6 shows simplified block diagram of an electronic device 600 in accordance with an embodiment of the invention. The electronic device 600 may correspond to a user's electronic device 220 explained with reference to FIG. 2. In some embodiments, the electronic device 600 may correspond to the system 200 explained with reference to FIGS. 2 to 5. The electronic device 600 is depicted to include a plurality of applications 606 which may include applications, such as the performance tracking application 228 explained with reference to FIG. 2

It should be understood that the electronic device 600 as illustrated and hereinafter described is merely illustrative of one type of device and should not be taken to limit the scope of the embodiments. As such, it should be appreciated that at least some of the components described below in connection with that the electronic device 600 may be optional and thus in an example embodiment may include more, less or different components than those described in connection with the example embodiment of the FIG. 6. As such, among other examples, the electronic device 600 could be any of an electronic device, for example, a wearable device such as fitness band, such a cellular phone, a tablet computer, a laptop, a mobile computer, a personal digital assistant (PDA), or any combination of the aforementioned, and other types of communication or multimedia devices.

The illustrated electronic device 600 includes a controller or a processor 602 (e.g., a signal processor, microprocessor, ASIC, or other control and processing logic circuitry) for performing such tasks as signal coding, data processing, image processing, input/output processing, power control, and/or other functions. An operating system 604 controls the allocation and usage of the components of the electronic device 600 and support for one or more applications programs (for example, the performance tracking application 228), that implements one or more of the innovative features related to tracking performance of physical activities of users described herein. The applications 606 may include common mobile computing applications (e.g., telephony applications, email applications, calendars, contact managers, web browsers, messaging applications such as USSD messaging or SMS messaging or SIM Tool Kit (STK) application) or any other computing application.

The illustrated electronic device 600 includes one or more memory components, for example, a non-removable memory 608 and/or a removable memory 610. The non-removable memory 608 and/or the removable memory 610 may be collectively known as database in an embodiment. The non-removable memory 608 can include RAM, ROM, flash memory, a hard disk, or other well-known memory storage technologies. The removable memory 610 can include flash memory, smart cards, or a Subscriber Identity Module (SIM). The one or more memory components can be used for storing data and/or code for running the operating system 604 and the applications 606. The electronic device 600 may further include a user identity module (UIM) 612. The UIM 612 may be a memory device having a processor built in. The UIM 612 may include, for example, a subscriber identity module (SIM), a universal integrated circuit card (UICC), a universal subscriber identity module (USIM), a removable user identity module (R-UIM), or any other smart card. The UIM 612 typically stores information elements related to a mobile subscriber. The UIM 612 in form of the SIM card is well known in Global System for Mobile Communications (GSM) communication systems, Code Division Multiple Access (CDMA) systems, or with third-generation (3G) wireless communication protocols such as Universal Mobile Telecommunications System (UMTS), CDMA2000, wideband CDMA (WCDMA) and time division-synchronous CDMA (TD-SCDMA), or with fourth-generation (4G) wireless communication protocols such as LTE (Long-Term Evolution).

The electronic device 600 can support one or more input devices 620 and one or more output devices 630. Examples of the input devices 620 may include, but are not limited to, a touch screen/a display screen 622 (e.g., capable of capturing finger tap inputs, finger gesture inputs, multi-finger tap inputs, multi-finger gesture inputs, or keystroke inputs from a virtual keyboard or keypad), a microphone 624 (e.g., capable of capturing voice input), a camera module 626 (e.g., capable of capturing still picture images and/or video images of surrounding environment) and a physical keyboard 628. Examples of the output devices 630 may include but are not limited to a speaker 632 and a display 634. The display 634 may be configured to display UIs associated with a performance tracking application. Other possible output devices can include piezoelectric or other haptic output devices. Some devices can serve more than one input/output function. For example, the touch screen 622 and the display 634 can be combined into a single input/output device.

A wireless modem 640 can be coupled to one or more antennas (not shown in the FIG. 6) and can support two-way communications between the processor 602 and external devices, as is well understood in the art. The wireless modem 640 is shown generically and can include, for example, a cellular modem 642 for communicating at long range with the mobile communication network, a Wi-Fi compatible modem 644 for communicating at short range with an external Bluetooth-equipped device or a local wireless data network or router, and/or a Bluetooth-compatible modem 646. The wireless modem 640 is typically configured for communication with one or more cellular networks, such as a GSM network for data and voice communications within a single cellular network, between cellular networks, or between the electronic device 600 and a public switched telephone network (PSTN).

The electronic device 600 can further include one or more input/output ports 650, a power supply 652, one or more sensors 654 configuring a sensor unit such as the sensor unit 224 explained with reference to FIG. 2, a transceiver 656 (for wirelessly transmitting analog or digital signals) and/or a physical connector 660, which can be a USB port, IEEE 1294 (FireWire) port, and/or RS-232 port. The illustrated components are not required or all-inclusive, as any of the components shown can be deleted and other components can be added.

Various embodiments disclosed herein provide numerous advantages. The techniques disclosed herein provide a system (such as, the system 200) and method (such as, the method 500) for measuring performance of a physical activity performed by a user. The system 200 and the method 500 provide visual feedback to the user while performing the physical activity (e.g., during the run) itself, thus allowing the user to adjust training methodologies in real-time. The system 200 is easy to deploy and relatively cost-effective to setup, while being easily transportable, thus allowing the user to have freedom to perform training for the physical activity at location of his/her choice. The system 200 can also record the physical activity from user's point of view for later retrieval and analysis.

Further, the performance data of the user may be used to generate feedback for the user to facilitate better performance of actions of the particular action-type. A current skill level of the user may be determined based on the athletic-performance model. The current skill level may be quantified as a measure of one or more variances of one or more action parameters of the particular action-type. Target ranges of action-parameter values may be determined, based on the athletic-performance model. Each target range may be based there being a computed probability that, given an action completed with action-parameter values in the target ranges, the user will have a positive outcome for the action.

Various embodiments described above may be implemented in software, hardware, application logic or a combination of software, hardware and application logic. The software, application logic and/or hardware may reside on one or more memory locations, one or more processors, an electronic device or, a computer program product. In an embodiment, the application logic, software or an instruction set is maintained on any one of various conventional computer-readable media. In the context of this document, a "computer-readable medium" may be any media or means that can contain, store, communicate, propagate or transport the instructions for use by or in connection with an apparatus, as described and depicted in FIG. 2. A computer-readable medium may include a computer-readable storage medium that may be any media or means that can contain or store the instructions for use by or in connection with an instruction execution system, system, or device, such as a computer.

Although the present invention has been described with reference to specific exemplary embodiments, it is noted that various modifications and changes may be made to these embodiments without departing from the broad spirit and scope of the present invention. For example, the various operations, blocks, etc., described herein may be enabled and operated using hardware circuitry (for example, complementary metal oxide semiconductor (CMOS) based logic circuitry), firmware, software and/or any combination of hardware, firmware, and/or software (for example, embodied in a machine-readable medium). For example, the apparatuses and methods may be embodied using transistors, logic gates, and electrical circuits (for example, application specific integrated circuit (ASIC) circuitry and/or in Digital Signal Processor (DSP) circuitry).

Particularly, the system 200 and its various components such as the controller 202, the memory 204, the visual aid unit 206 and the communication unit 208 may be enabled using software and/or using transistors, logic gates, and electrical circuits (for example, integrated circuit circuitry such as ASIC circuitry). Various embodiments of the present invention may include one or more computer programs stored or otherwise embodied on a computer-readable medium, wherein the computer programs are configured to cause a processor or computer to perform one or more operations (for example, operations explained herein with reference to FIG. 6). A computer-readable medium storing, embodying, or encoded with a computer program, or similar language, may be embodied as a tangible data storage device storing one or more software programs that are configured to cause a processor or computer to perform one or more operations. Such operations may be, for example, any of the steps or operations described herein. In some embodiments, the computer programs may be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), DVD (Digital Versatile Disc), BD (Blu-ray (registered trademark) Disc), and semiconductor memories (such as mask ROM, PROM (programmable ROM), EPROM (erasable PROM), flash ROM, RAM (random access memory), etc.). Additionally, a tangible data storage device may be embodied as one or more volatile memory devices, one or more non-volatile memory devices, and/or a combination of one or more volatile memory devices and non-volatile memory devices. In some embodiments, the computer programs may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

Various embodiments of the present invention, as discussed above, may be practiced with steps and/or operations in a different order, and/or with hardware elements in configurations, which are different than those which, are disclosed. Therefore, although the invention has been described based upon these exemplary embodiments, it is noted that certain modifications, variations, and alternative constructions may be apparent and well within the spirit and scope of the invention.

Although various exemplary embodiments of the present invention are described herein in a language specific to structural features and/or methodological acts, the subject matter defined in the appended claims is not necessarily limited to the specific features or acts described above. Rather, the specific features and acts described above are disclosed as exemplary forms of implementing the claims.

The invention claimed is:

1. A system for tracking performance of a physical activity of a user on a field, the system comprising:
   a visual aid unit; and
   a controller in operable communication with the visual aid unit, the controller configured to:
   receive sensor data indicative of at least one of position and direction of movement of the user on the field, the sensor data generated in relation to a first performance of the physical activity by the user,
   analyze the sensor data to generate visual indicators for the user, and
   control the visual aid unit to project the generated visual indicators during a second performance of the physical activity by the user for reference of the user, the visual indicators configured to aid in improving the performance of the user in relation to the physical activity.

2. The system as claimed in claim 1, wherein the system is located in an unmanned vehicle capable of traversing the field.

3. The system as claimed in claim 2, wherein the controller is configured to control the unmanned vehicle to traverse the field based, at least in part, on the sensor data to effectively follow the direction of the movement of the user during the second performance of the physical activity by the user.

4. The system as claimed in claim 3, wherein the visual aid unit is configured to project the generated visual indicators on the field proximal to the position of the user during the second performance of the physical activity by the user.

5. The system as claimed in claim 4, wherein the unmanned vehicle is an unmanned aerial vehicle.

6. The system as claimed in claim 1, wherein the sensor data is generated by a sensor unit placed within an electronic device associated with the user and, wherein the electronic device is in operable communication with the system for providing the sensor data to the controller.

7. The system as claimed in claim 6, wherein the sensor unit comprises at least one inertial sensor and at least one position sensor.

8. The system as claimed in claim 3, further comprising an imaging unit installed on the unmanned vehicle, wherein the imaging unit is configured to record the first performance and the second performance of the physical activity of the user.

9. A computer-implemented method for tracking performance of a physical activity of a user on a field, the method comprising:
   receiving, by a system, sensor data indicative of at least one of position and direction of movement of the user on the field, the sensor data generated in relation to a first performance of the physical activity by the user;
   analyzing, by the system, the sensor data to generate visual indicators for the user; and
   projecting, by the system, the generated visual indicators during a second performance of the physical activity by the user for reference of the user, the visual indicators configured to aid in improving the performance of the user in relation to the physical activity.

10. The method as claimed in claim 9, wherein the system is located in an unmanned vehicle capable of traversing the field.

11. The method as claimed in claim 10, further comprising:
    controlling, by the system, the unmanned vehicle to traverse the field based, at least in part, on the sensor data to effectively follow the direction of the movement of the user during the second performance of the physical activity by the user.

12. The method as claimed in claim 11, wherein the generated visual indicators are projected on the field proximal to the position of the user during the second performance of the physical activity by the user.

13. The method as claimed in claim 12, wherein the unmanned vehicle is an unmanned aerial vehicle.

14. The method as claimed in claim 10, further comprising:
    recording, by the system, the first performance and the second performance of the physical activity of the user.

15. The method as claimed in claim 9, wherein the sensor data is generated by a sensor unit placed within an electronic device associated with the user and, wherein the electronic device is in operable communication with the system for providing the sensor data to the system.

16. The method as claimed in claim 15, wherein the sensor data comprises inertial movement information and location information of the user on the field.

17. An unmanned vehicle for tracking performance of a physical activity of a user on a field, the unmanned vehicle capable of traversing the field, the unmanned vehicle comprising:
  a visual aid unit;
  a communication unit in operable communication with an electronic device associated with the user for receiving sensor data indicative of at least one of position and direction of movement of the user on the field, the sensor data generated in relation to a first performance of the physical activity by the user; and
  a controller in operable communication with the visual aid unit and the communication unit, the controller configured to:
    analyze the sensor data to generate visual indicators for the user,
    control the unmanned vehicle to traverse the field based, at least in part, on the sensor data to effectively follow the direction of the movement of the user during a second performance of the physical activity by the user, and
    control the visual aid unit to project the generated visual indicators during the second performance of the physical activity by the user for reference of the user, the visual indicators configured to aid in improving the performance of the user in relation to the physical activity.

18. The unmanned vehicle as claimed in claim 17, wherein the sensor data is generated by a sensor unit placed within the electronic device and, wherein the sensor data comprises inertial movement information and location information of the user on the field.

19. The unmanned vehicle as claimed in claim 17, further comprising an imaging unit configured to record the first performance and the second performance of the physical activity of the user.

20. The unmanned vehicle as claimed in claim 19, wherein the unmanned vehicle is an unmanned aerial vehicle.

* * * * *